(12) United States Patent
Hall et al.

(10) Patent No.: US 8,841,270 B2
(45) Date of Patent: Sep. 23, 2014

(54) USE OF INHIBITORS OF ZDHHC2 ACTIVITY FOR MODULATION OF ADIPOGENESIS

(75) Inventors: Diana Hall, Lausanne (CH); Maria Jimenez, Chavannes-Pres-Renens (CH); Carine Poussin, Evian-les-Bains (FR); Bernard Thorens, Epalinges (CH)

(73) Assignee: Sanofi, Paris (FR)

(*) Notice: Subject to any disclaimer, the term of this patent is extended or adjusted under 35 U.S.C. 154(b) by 127 days.

(21) Appl. No.: 13/321,013

(22) PCT Filed: May 19, 2010

(86) PCT No.: PCT/IB2010/052225
§ 371 (c)(1),
(2), (4) Date: Mar. 7, 2012

(87) PCT Pub. No.: WO2010/134032
PCT Pub. Date: Nov. 25, 2010

(65) Prior Publication Data
US 2012/0165391 A1    Jun. 28, 2012

(30) Foreign Application Priority Data

May 20, 2009 (EP) .................................... 09305467

(51) Int. Cl.
| | | |
|---|---|---|
| *A61K 31/70* | (2006.01) | |
| *C07H 21/02* | (2006.01) | |
| *C07H 21/04* | (2006.01) | |
| *C12N 15/113* | (2010.01) | |
| *A61K 31/7105* | (2006.01) | |
| *A61K 31/713* | (2006.01) | |
| *C12Q 1/68* | (2006.01) | |

(52) U.S. Cl.
CPC .......... *C12N 15/113* (2013.01); *A61K 31/7105* (2013.01); *A61K 31/713* (2013.01); *C12N 2310/14* (2013.01)
USPC ....... 514/44 A; 536/23.1; 536/24.1; 536/24.5; 435/377

(58) Field of Classification Search
None
See application file for complete search history.

(56) References Cited

FOREIGN PATENT DOCUMENTS

WO    WO 02/24884 A    3/2002

OTHER PUBLICATIONS

Planey et al., Molecular Biology of the Cell vol. 20:1454-1463, Mar. 1, 2009.*
Jennings et al., Journal of Lipid Research vol. 50:233-242, 2009.*
Amkri, et al. Fatty acids as signal transducing molecules: involvement in the differentiation of preadipose to adipose cells; J Lipid Res; 1994, vol. 35, No. 5, pp. 930-937.
Sharma, et al: DHHC2 Affects Palmitoylation, Stability, and Functions of Tetraspanins CD9 and CD151; Mol Bio Cell; 2008, vol. 19, pp. 3415-3425.
Zhang, et al: Identification of CKAP4/p63 as a Major Substrate of the Palmitoyl Acyltransferase DHHC2, a Putative Tumor Suppressor, Using a Novel Proteomics Method; MCP, 2008, vol. 7, No. 7, pp. 1378-1388.
International Search Report, PCT/IB2010/052225, dated Aug. 18, 2010, 5 pages.
International Preliminary Report on Patentability, PCT/IB2010/052225, dated Nov. 22, 2011, 9 pages.

* cited by examiner

*Primary Examiner* — Sean McGarry
(74) *Attorney, Agent, or Firm* — Lathrop & Gage LLP; James H. Velema, Esq.

(57) ABSTRACT

The present invention concerns Zdhhc2, a new target involved in adipogenesis modulation. Using a siRNA approach, the inventors demonstrated that decrease in Zdhhc2 activity in adipose tissue induces a decrease in adipogenesis. Thus, the present invention relates to modulators of Zdhhc2 activity as well as screening test for identification of modulators of the activity of this target, and their use, especially in pharmaceutical composition, to modulate adipogenesis and thus treat obesity and related disorders.

9 Claims, 5 Drawing Sheets

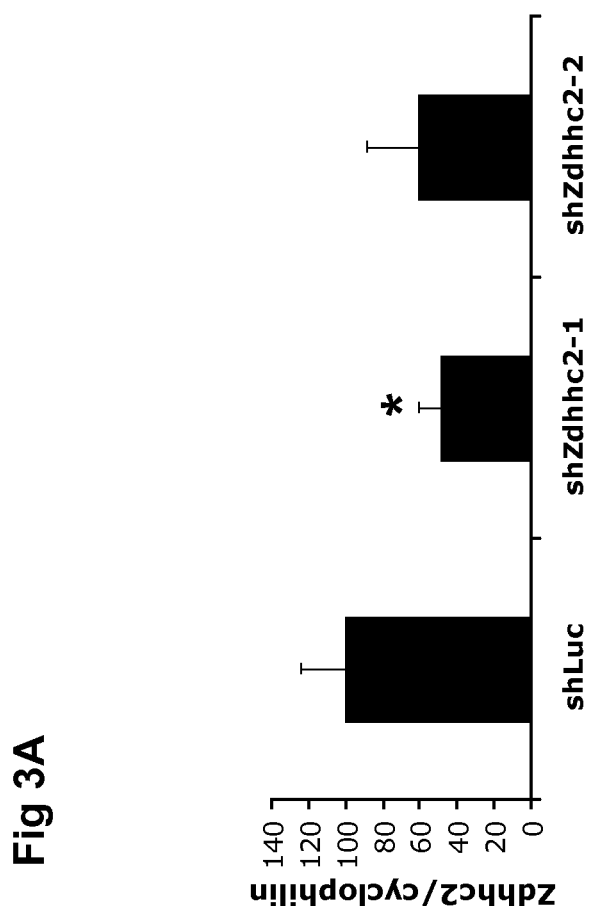

USE OF INHIBITORS OF ZDHHC2 ACTIVITY FOR MODULATION OF ADIPOGENESIS

The present invention concerns Zdhhc2, a new target involved in adipogenesis modulation as well as screening test for identification of modulators of the activity of this target. Further, the present invention relates to modulators of Zdhhc2 activity and their use, especially in pharmaceutical composition, to modulate adipogenesis and thus to treat obesity and related disorders.

Obesity is a major risk factor for a number of disorders including hypertension, coronary artery disease, dyslipidemia, insulin resistance and type 2 diabetes. Because of the importance of the obesity epidemic, a great deal of investigation has centered on the biology of the adipocyte, including the developmental pathway by which new adipocytes are created. Adipogenesis is the process by which undifferentiated mesenchymal precursor cells become mature adipocytes. Throughout the last decade considerable progress has been made in elucidating the molecular mechanisms of adipocyte differentiation, which involve sequential activation of transcription factors from several families such as CCAAT/enhancer binding proteins (C/EBPα, α, and γ) and the nuclear hormone receptor peroxisome proliferator-activated receptor γ (PPARγ) (Rosen, E. D. et al., 2002). PPARγ is described as a "master regulator" of adipogenesis since it has been shown to be both sufficient and necessary for adipogenesis both in vitro and in vivo. Recently, new transcription factors have been described to participate in adipogenesis such as KLF family (KLF2, 5 and KLF15) (Banerjee, S. S. et al., 2003; Gray, S. M. et al., 2002), Ebf family (Jimenez, M. A. et al., 2007) and Krox 20 (Chen, Z. et al., 2005), suggesting that the transcriptional cascade occurring during adipogenesis is much more complex than previously thought. Furthermore, signaling molecules and/or receptors such as the Wnt family of secreted proteins (Kang S. et al., 2007), sonic hedgehog protein, Notch receptor have also been described to be involved in molecular events leading to adipocyte formation.

These last years, an emerging concept has linked the molecular events leading to adipocyte development to the extracellular matrix (ECM) remodeling in the developing fat pad. Indeed, the developing mesenchymal cell undergoes a dramatic alteration of cell morphology from stelate-shaped to sphere. These changes in cell morphology are paralleled by dramatic changes in the levels and the types of cytoskeletal, extracellular matrix and related components such as actin, fibronectin and collagen (Grégoire F. M. et al., 1998; Hausman, G. J. et al. 1996). Interestingly, adipose tissue contains a rich ECM, whose composition varies throughout life with changes in fat mass (Chun, T. et al., 2006; Gagnon, A. M., J. et al. 1998; Mehlhorn, A. T., P et al., 2006; Nakajima, I. S. et al. 2002).

The ECM not only influences the integrity of the structural system that supports cells, but also influences, via cell-surface receptors, cell-cell and cell-matrix interactions the molecular and signaling events that take place in the cells during the differentiation process. Thus, extracellular and intracellular events are coupled to regulate adipogenesis.

Storage of fat in adipose tissue is limited and exceeding this capacity leads to accumulation of lipids in others tissues, in particular in muscle, liver, and the endocrine pancreas, and to the secretion by adipocytes of various adipokines. The adipose tissue consists of several deposits located at different anatomical sites which may originate from distinct precursors and which have different physiological functions and pathophysiological roles. The visceral, as opposed to the subcutaneous adipose depots, may contribute more to the defects associated with the metabolic syndrome.

Cannabinoid 1 receptors have been identified in all organs playing a key role in glucose metabolism and type 2 diabetes, i.e. adipose tissue, the gastrointestinal tract, the liver, the skeletal muscle and the pancreas. Rimonabant, the first selective cannabinoid receptor 1 (CB1R) antagonist in clinical use, has been shown to reduce food intake and body weight thus improving glucose metabolism regulation.

However, there is still a need for novel therapeutic targets for the treatment of obesity.

Zinc finger, DHHC-type containing 2 proteins (Zdhhc2) has a palmitoyltransferase activity, and adds palmitic acid moiety to membrane receptors, integrin, caveolin and Wnt proteins (Oyama, T. et al., 2000; Fukumura, D. et al., 2003). As described above, Wnt proteins are involved in adipogenesis.

The inventors have now found that Zdhhc2 plays a critical role in adipocytes differentiation.

They propose that this enzyme is involved in adipocyte development by modifying signaling molecules or extracellular matrix proteins such as integrin. Extracellular matrix plasticity has recently been proposed to play an important role, not only for tissue integrity, but also for adipose tissue development. Therefore, Zdhhc2 might have a greater impact on extracellular matrix component and might have a role in the 3-dimensional development of adipose tissue. Furthermore, this protein is located at the cell membrane and could be a potential target for new drugs development.

Zdhhc2 is thus considered as a new relevant target for modulation of adipogenesis and for the treatment of obesity and related disorders. Inhibition of Zdhhc2 can also be used to decrease adipogenesis for reduction of subcutaneous and visceral fat accumulation.

DETAILED DESCRIPTION OF THE INVENTION

The present invention is dawn to methods for regulating adipogenesis and metabolic function in adipocytes.

The present invention consists in the use of inhibitors of Zdhhc2 activity for modulation of adipogenesis, in particular for treatment of obesity and related disorders. The invention also concerns pharmaceutical composition containing such modulators of adipogenesis and related disorders and screening test for such modulators.

Through a transcriptomic approach, the inventors identified genes whose expression was correlated with body weight gain in cohorts of C57BI/6 mice fed a high fat diet. Then, they conducted a second analysis in order to evaluate the changes in gene expression induced by rimonabant treatment of the high fat diet fed mice. Genes which have never been described before in adipocyte biology, but which might be involved in important biological processes such as signaling, modification of extracellular matrix proteins, and gene transcription were retained. These genes could be important for adipogenesis especially since they might be involved in the mechanism by which rimonabant reduces fat mass in mice. In this context, Zdhhc2 was identified as involved in adipocytes metabolism, especially as a major player of extracellular matrix component modulation in link with the 3-dimensional development of adipose tissue. More generally, this gene appears to play a role in adipogenesis and control of adipose tissue development in obesity.

The present invention consists in identification of modulators of Zdhhc2 activity. Such modulators can be any compound or molecule able to modulate Zdhhc2 activity in particular small molecules, lipids and siRNA.

Modulators of Zdhhc2 activity can be identified by detecting the ability of an agent to modulate the activity of Zdhhc2. Inhibitors of Zdhhc2 are any compound able to reduce or inhibit, totally or partially, the activity of Zdhhc2. Inhibitors of Zdhhc2 include, but are not limited to, agents that interfere with the interaction of Zdhhc2 with its natural partner in the intracellular compartment and agents that reduce Zdhhc2 expression, both at transcriptional and translational levels.

CD9 and CD151 are two membrane proteins which specifically and directly interact with Zdhhc2. These proteins are able to bind integrins after palmytoylation by Zdhhc2 then allowing cell-cell attachment as described in Resh, M D et al. (2006) and Sharma C., et al. (2008). Therefore, modulators of Zdhhc2 activity can be tested in a screening that would be based on the presence on CD9 or CD151 of labeled palmitate residue due to the Zdhhc2 activity.

As an example, in one particular, embodiment a screening test can be performed as follows: membrane fraction from recombinant cells expressing CD9 or CD151 are prepared. This fraction is incubated with a sample containing Zdhhc2 activity (any source is suitable as extract from adipose tissue from patients, from animals or from recombinant cells) as well as labeled palmitate (as $^3$H palmitate) and a candidate compound. Then the palmitoylation activity of Zdhhc2 is measured by the quantification of labeled palmitate present on the target protein. For this step, the target protein (CD9, CD151 or any specific target for Zdhhc2) are immunoprecipitated using a specific antibody. The $^3$H emission detected in the retained fraction is quantified. As a result, the quantity of signal detected is proportional to the activity of Zdhhc2 present in the sample. Therefore, an inhibitor compound can be identified when a decrease in Zdhhc2 activity is measured compared to a control sample containing no candidate compound.

In another embodiment, the expression of Zdhhc2 is modulated through RNA interference, using small interfering RNAs (siRNA) or small hairpin RNAs (shRNAs). Therefore, in one aspect, the present invention relates to double stranded nucleic acid molecules including small nucleic acid molecules, such as short interfering nucleic acid (siNA), short interfering RNA (siRNA), double-stranded RNA (dsRNA), micro-RNA (miRNA), and short hairpin RNA (shRNA) molecules able to mediate RNA interference (RNAi) against Zdhhc2 gene expression, including cocktails of such small nucleic acid molecules and suitable formulations of such small nucleic acid molecules.

The phenomenon of RNAi mediated gene silencing has been described first in the *Caenorhabditis elegans* system, in which microinjection of long double stranded RNA molecules was reported. The mechanism of RNA mediated gene inactivation seems to be slightly different in the various organisms that have been investigated so far. However, in all systems, RNA mediated gene silencing is based on post-transcriptional degradation of the target mRNA induced by the endonuclease Argonaute2 which is part of the so called RISC complex. Sequence specificity of degradation is determined by the nucleotide sequence of the specific antisense RNA strand loaded into the RISC complex.

The introduction into cells of a siRNA compound results in cells having a reduced level of the target mRNA and, thus, of the corresponding polypeptide and, concurrently, of the corresponding enzyme activity.

siRNAs specific for Zdhhc2, as described herein, can be used as modulators of Zdhhc2 activity, in order to reduce the translation of Zdhhc2 mRNA. More particularly, siRNA specific for Zdhhc2 can be used to reduce adipogenesis and thus to treat obesity and related diseases.

In one embodiment, the invention features a double stranded nucleic acid molecule, such as a siRNA molecule, where one of the strands comprises nucleotide sequence having complementarity to a predetermined Zdhhc2 nucleotide sequence in a target Zdhhc2 nucleic acid molecule, or a portion thereof.

The RNA molecule can be used modified or unmodified. An example of modification is the incorporation of tricylo-DNA to allow improved serum stability of oligonucleotide.

In one embodiment, the predetermined Zdhhc2 nucleotide sequence is a Zdhhc2 nucleotide target sequence described herein (SEQ ID NO. 1 and SEQ ID NO. 3).

Due to the potential for sequence variability of the genome across different organisms or different subjects, selection of siRNA molecules for broad therapeutic applications likely involves the conserved regions of the gene. Thus in one embodiment, the present invention relates to siRNA molecules that target conserved regions of the genome or regions that are conserved across different targets. siRNA molecules designed to target conserved regions of various targets enable efficient inhibition of Zdhhc2 gene expression in diverse patient populations.

In one embodiment, the invention features a double-stranded short interfering nucleic acid molecule that down-regulates expression of a target Zdhhc2 gene or that directs cleavage of a target RNA, wherein said siRNA molecule comprises about 15 to about 28 base pairs, preferably 19 base pairs. A siRNA or RNAi inhibitor of the instant invention can be chemically synthesized, expressed from a vector or enzymatically synthesized.

In a particular embodiment, the siRNA specific for Zdhhc2 are shRNA having sequence SEQ ID NO. 5 or SEQ ID NO. 6. In a preferred embodiment, the siRNA specific for Zdhhc2 are shRNA having sequence SEQ ID NO. 5. The use of a siRNA according to the present invention leads to reduction of the mRNA level from 5% to 20%, preferably from 5% to 15%, more preferably from 5% to 10% of the mRNA level of the corresponding wild type cell. The wild type cell is the cell prior to the introduction of the nucleic acid encoding the siRNA compound, in which the targeted mRNA is not degraded by a siRNA compound.

Inhibitors of Zdhhc2 activity can be administered by any suitable route, both locally or systemically depending on the nature of the molecule and the expected effect. SiRNA can be administrated locally in case of double strand molecule directly in the targeted tissue, or administrated through a vector in case of shRNA, according to protocols used in the art.

In one embodiment, RNAi is obtained using shRNA molecules. ShRNA constructs encode a stem-loop RNA. After introduction into cells, this stem-loop RNA is processed into a double stranded RNA compound, the sequence of which corresponds to the stem of the original RNA molecule. Such double stranded RNA can be prepared according to any method known in the art including vitro and in vivo methods as, but not limited to, described in Sahber et al (1987), Bhattacharyya et al, (1990) or U.S. Pat. No. 5,795,715.

For in vivo administration, shRNA can be introduced into a plasmid. Plasmid-derived shRNAs present the advantage to provide the option for combination with reporter genes or selection markers, and delivery via viral or non viral vectors. The introduction of shRNA into a vector and then into cells ensure that the shRNA is continuously expressed. The vector is usually passed on to daughter cells, allowing the gene silencing to be inherited.

The present invention also provides vectors comprising the polynucleotides for expression of shRNA expression of the invention. These vectors are for example AAV vector, retroviral vector in particular lentiviral vector, adenoviral vector which can be administered by different suitable routes including intravenous route, intramuscular route, direct injection into subcutaneous tissue or other targeted tissue chosen according to usual practice.

The route of administration of siRNA varies from local, direct delivery to systemic intravenous administration. The advantage of local delivery is that the doses of siRNA required for efficacy are substantially low since the molecules are injected into or near the target tissue. Local administration also allows for focused delivery of siRNA. For such direct delivery, naked siRNA can be used. "Naked siRNA" refers to delivery of siRNA (unmodified or modified) in saline or other simple excipients such as 5% dextrose. The ease of formulation and administration of such molecules makes this an attractive therapeutic approach. Naked DNA can also be formulated into lipids especially liposomes.

Systemic application of siRNA is often less invasive and, more importantly, not limited to tissues which are sufficiently accessible from outside. For systemic delivery, siRNA can be formulated with cholesterol conjugate, liposomes or polymer-based nanoparticules. Liposomes are traditionally used in order to provide increased pharmacokinetics properties and/or decreased toxicity profiles. They allow significant and repeated success in vivo delivery. Currently, use of lipid-based formulations of systemic delivery of siRNA, especially to hepatocytes, appears to represent one of the most promising near-term opportunities for development of RNAi therapeutics. Formulation with polymers such as dynamic polyconjugates—for example coupled to N-acetylglucosamine for hepatocytes targeting—and cyclodextrin-based nanoparticules allow both targeted delivery and endosomal escape mechanisms. Others polymers such as atelocollagen and chitosan allow therapeutic effects on subcutaneous tumor xenografts as well as on bone metastases.

SiRNA can also be directly conjugated with a molecular entity designed to help targeted delivery. Given the nature of the siRNA duplex, the presence of the inactive or sense stand makes for an ideal site for conjugation. Examples of conjugates are lipophilic conjugates such as cholesterol, or aptamer-based conjugates.

Cationic peptides and proteins are also used to form complexes with the negatively charged phosphate backbone of the siRNA duplex.

These different delivery approaches can be used to target the Zdhhc2 siRNA into the relevant tissue, especially adipose tissue. For such targeting, siRNA can be conjugated to different molecules interacting with pre-adipocytes and adipocytes, as for example ligands interacting with lipids transporters, receptors, insulin receptor or any molecule known in the art.

Another object of the invention is a pharmaceutical composition, which comprises, as active principle, a modulator of Zdhhc2 according to the present invention. These pharmaceutical compositions comprise an effective dose of at least one modulator according to the invention, and at least one pharmaceutically acceptable excipient. Said excipients are chosen according to the pharmaceutical form and the administration route desired, among usual excipients known of one of skill in the art.

The invention also consists in a method for modulation of adipogenesis. Such method can be used to treat obesity or related diseases. Such method can also be used in order to decrease fat accumulation in a cosmetic purpose.

Modulators of Zdhhc2 activity are useful in therapeutics to modulate adipogenesis, in particular in the treatment and prevention of obesity related disorders, in particular type 2 diabetes, dyslipidemia, elevated blood pressure, insulin resistance, cardiovascular disorders and more generally metabolic syndromes.

The present invention, according to another of its aspects, relates to a method for the treatment of the above pathologies, which comprises the in vivo administration to a patient of an effective dose of a modulator of Zdhhc2 according to the invention.

The appropriate unitary dosage forms comprise the oral forms, such as tablets, hard or soft gelatin capsules, powders, granules and oral solutions or suspensions, the sublingual, buccal, intratracheal, intraocular, intranasal forms, by inhalation, the topical, transdermal, sub-cutaneous, intramuscular or intra-venous forms, the rectal forms and the implants. For the topical application, the compounds of the invention may be used as creams, gels, ointments or lotions.

According to usual practice, the dosage suitable to each patient is determined by the physician according to the administration route, the weight and response of the patient.

Zdhhc2 inhibitors are also useful for cosmetic applications in order to reduce disgraceful fat accumulation.

For cosmetic applications, inhibitors of Zdhhc2 can be incorporated in a suitable formulation for topical use. The inhibitors of Zdhhc2 can both be small molecules or siRNA as previously described.

The invention is now described by reference to the following examples, which are illustrative only, and are not intended to limit the present invention.

MATERIAL AND METHODS

Animals Treatment

Figure 1A:
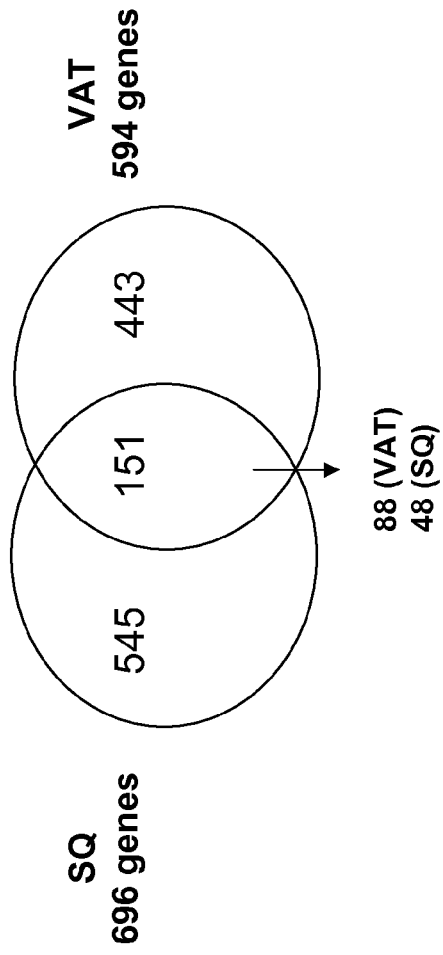
FIG. 1: Selection of critical adipose tissue regulatory genes. The Venn diagrams illustrate the selection of genes based on the following criteria. A) Similar regulation by high fat feeding in subcutaneous (SCAT or Sq) and visceral (VAT). 151 genes were selected (48 for SCAT and 88 for VAT). B) Among those 151 genes, selection of genes regulated by rimonabant treatment (14 for SCAT and 54 for VAT). This led to the selection of 34 genes regulated in both tissues by high fat feeding and rimonabant. Among those genes, 16 have expression level correlated with body weight of L, M and H groups (obesity-linked) and 18 are regulated by HFD to the same level in each subgroup (not obesity-linked).

C57BL/6J mice, which are obesity-prone (5), were fed for 6 months with a high fat diet (HFD). After 6 months of HFD, mice exhibited scattered body weights with various degrees of glucose intolerance (measured by a glucose tolerance test. The HFD mice were separated into 3 groups displaying the same level of glucose intolerance but with low (L), medium (M) or high (H) body weights and treated them, as well as normal chow (NC) fed mice, for one month with vehicle or rimonabant (10 mg·kg$^{-1}$·day$^{-1}$), to normalize their body weight. The treatment also normalized glucose tolerance, as described previously (25).

RNA Preparation, Labeling and Hybridization on cDNA Microarrays.

RNA from 5 different mice per group was extracted from visceral and subcutaneous adipose tissues using peqGOLD Trifast™ (peqlab) and chloroform-isoamylalcool (24:1) extraction. RNA was precipitated with isopropanol and purified by passage over RNeasy columns (Qiagen). RNA quality was checked before and after amplification with a Bioanalyzer 2100 (Agilent). RNA was reverse transcribed and RNA was amplified with MessageAmp™ kit (Ambion). A Mouse Universal Reference (Clontech) was similarly amplified and both adipose tissue and reference RNAs were labeled by an indirect technique with Cy5 and Cy3 according to published protocols (de Fourmestraux et al., J. Biol. Chem. 2004 279: 50743-53). Labeled RNAs were hybridized to microarrays containing 17664 cDNAs prepared at the DNA Array Facility of the University of Lausanne. Scanning, image, and quality control analyses were performed as previously published (de Fourmestraux et al., J. Biol. Chem. 2004 279:50743-53). Data were expressed as log$_2$ intensity ratios (Cy5/Cy3), normalized with a print tip locally weighted linear regression (Lowess) method and filtered based on spot quality and incomplete annotation. All analyses were performed with the R software for statistical computing available at the Comprehensive R Archive Network (cran.us.r-project.org/).

Cell Culture

3T3-L1 cells were cultured in DMEM (Gibco) with 10% FBS (Gibco) at 5% $CO_2$. After retroviral infection (see below), cells were allow to grow to confluence in either 100-mm or 60-mm dishes in DMEM with 10% FBS. Once confluence was reached, cells were exposed to differentiation medium containing dexamethasone (1 µM), insulin (5 µg/ml), and isobutylmethylxanthine (0.5 µM) (DMI). After 2 days cells were maintained in medium containing insulin (5 µml) until ready for harvest at 7 days.

Oil-red-O Staining

After 7 to 10 days of differentiation, cells were washed once in PBS and fixed with formaldehyde (Formalde-fresh; Fisher) for 15 minutes. The staining solution was prepared by dissolving 0.5 g oil-red-0 in 100 ml of isopropanol; 60 ml of this solution was mixed with 40 ml of distilled water. After 1 hour at room temperature the staining solution was filtered and added to dishes for 4 hours. The staining solution was then removed and cells were washed twice with distilled water.

shRNA Constructs shRNAs were constructed using the RNAi-Ready pSIREN-RetroQ ZsGreen (Clontech). Target sequences for Zdhhc2 were designed by querying the Whitehead siRNA algorithm (http://jura.wi.mit.edu/bioc/siRNAext/) as well as the siRNA designer software from Clontech (http://bioinfo.clontech.com/rnaidesigner/); at least two sequences represented by both algorithms were subcloned into the pSIREN vectors (Clontech) using the EcoRI and BamH1 restriction sites. The following target sequences for Zdhhc2 were chosen SEQ ID NO. 5 and 6 as a negative control, we used the following siRNA sequence against luciferase: SEQ ID NO. 7.

Transfection of shRNA Constructs

The specificity of shRNAs was tested in 293T HEK cells co-transfected using calcium-Phosphate methods described in (14) with expression vectors containing Zdhhc2 cDNA and the RNAi-Ready pSIREN-RetroQ ZsGreen vector expressing either the shRNA against lucifeare (control shLUC) or Zdhhc2 (shZdhhc2). RT-PCR analysis was performed on cell RNA-extraction 24 h after transfection.

Generation of Retro Viral Constructs and Retro Viral Infections

Retroviruses were constructed in the RNAi-Ready pSIREN-RetroQ ZsGreen (pSIREN Clontech). Viral constructs were transfected using calcium-phosphate method described in Jordan, M. et al. (2004) into 293 HEK packaging cells along with constructs encoding gag-pol and the VSV-G protein. Supernatants were harvested after 48 h in presence of 3 µm of Trichostatin A (Sigma) and either used immediately or snap frozen and stored at −80° C. for later use. Viral supernatants were added to the cells for 6 hours in the presence of polybrene (4 µg/ml) and diluted two times with fresh medium for the next 15 hours.

Isolation of Adipocytes and Stromal Vascular Fraction (SVF) from Adipose Tissue

Eight week-old male C57BL/6J mice (n=6-8) were euthanized by $CO_2$ inhalation and epididymal (visceral) and subcutaneous adipose tissue were collected and placed in DMEM medium containing 10 mg/mL fatty acid-poor BSA (Sigma-Aldrich, St. Louis, Mich.). The tissue was minced into fine pieces and then digested in 0.12 units/mL collagenase type I (Sigma) at 37° C. in a shaking water bath (80 Hz) for 1 hour. Samples were then filtered through a sterile 250 µm nylon mesh (Scrynel NY250HC, Milian) to remove undigested fragments. The resulting suspension was centrifuged at 1100 RPM for 10 min to separate SVF from adipocytes. Adipocytes were removed and washed with DMEM buffer. They were then suspended in peqGOLD TriFast reagent (Axonlab) and RNA was isolated according to the manufacturer's instructions. The SVF fraction was incubated in erythrocyte lysis buffer (0.154 mM NH$_4$Cl, 10 mM KHCO$_3$, 0.1 mM EDTA) for 2 min. Cells were then centrifuged at 1100 RPM for 10 min and re-suspended in 500 µl of peqGOLD TriFast reagent (Axonlab) for RNA isolation.

RNA Extraction and Real-Time PCR

Total RNA was isolated from cultured cells using peqGOLD TriFast reagent according to the manufacturer's instructions (Axonlab). First strand cDNA was synthesized from 0.5 µg of total RNA using random primers and Superscript II (Invitrogen). Real time PCR was performed using Power SYBR Green Mix (Applied Biosystem). The following primers were used for mouse genes: mZdhhc2-F (SEQ ID NO. 8) and mZdhhc2-R (SEQ ID NO.9) for Zdhhc2; Ap2-F (SEQ ID NO. 16); Ap2-R (SEQ ID NO. 17) for; mCyclophilinA-F (SEQ ID NO. 12); mCyclophilinA-R (SEQ ID NO. 13), mCyclophilin A-F (SEQ ID NO.12); mCyclophilin A-R (SEQ ID NO. 13). The following primers were used for human genes: hZdhhc2-F SEQ ID NO. 10; hZdhhc2-R SEQ ID NO. 11 hCyclophilin A-F SEQ ID NO. 14; hCyclophilin A-R SEQ ID NO. 15.

Northern Blot

Total RNA from various mouse tissues was isolated using the peqGOLD TriFast reagent according to the manufacturer's instructions (Axonlab). Total RNA (8 µg) was separated on a 1.2% agarose/formaldehyde gel and transfected overnight to a nylon membrane. To control for RNA quantity loading, the membrane was stained with methylene blue prior the subsequent hybridizations. For the detection of Zdhh2 signals, probes from the full-length cDNA mouse plasmid (Open Biosystem) were used. The probes were labeled by random priming with [α-32P]dCTP (Amersham). Hybridization and washing were carried out using the Quickhib method according to manufacturer's instructions (Stratagene). Blots were exposed to Hyperfilm ECL (Amersham) at −80° C. for 1 day or several days depending on the signal intensity.

RESULTS

Example 1

Microarray Results

Figure 1B:
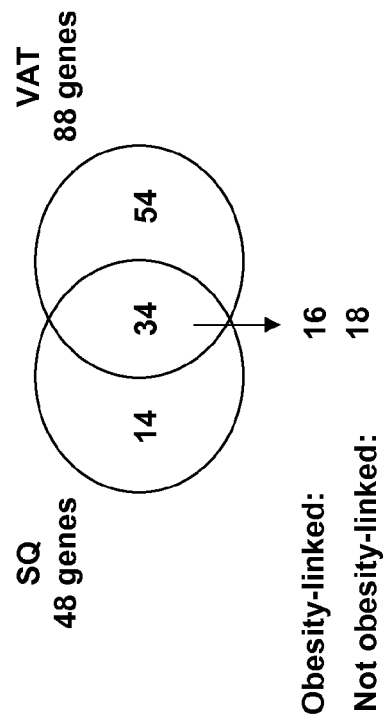

Bioinformatic analysis of the microarray data was performed to identify genes that fulfilled the three following criteria: (i) regulated by high fat feeding, (ii) similar regulated expression by high fat feeding in both visceral (VAT) and subcutaneous fat (SCAT) and (iii) similar normalization of their expression by rimonabant treatment (FIG. 1). Out of the ~17,000 gene targets present on the cDNA microarray used, 34 genes fulfilled these criteria, which are listed in Table 1. Remarkably, 10 of these genes—Cav1, Fgf1, Fndc3b, Kif5b, Mest, Npr3, Pik3ca, Sparc, Vldlr, and Wwtr1—were previously known to be important regulators of adipose tissue development and function. Some of these genes had expression levels correlated with body weight gain (shown in grey in Table 1), suggesting a potential role in hyperplasia and/or hypertrophy of adipose tissues during obesity. These results validate the approach used to identify possible novel targets for therapeutic treatment of obesity.

Most importantly, many of the genes cited in table 1 have never been studied in the context of in adipose tissue development or biology. These genes belong to the following classes of function: extracellular matrix/cell interaction, cytoskeleton, intracellular signaling, enzymes, and transcription factors/co-factors. They are likely involved in tissue remodeling, and particularly in adipocyte development. One of these genes, Zdhhc2 gene and it role in adipocyte biology, is presented herein and constitutes one aspect of the present invention.

Zdhhc2 has a palmitoyltransferase activity, and adds palmitic acid moiety to membrane receptors, integrin, caveolin and Wnt proteins (23, 6). Wnt proteins are involved in adipogenesis. Thus, this enzyme might be involved in adipocyte development by modifying signaling molecules or extracellular matrix proteins such as integrin. Extracellular matrix plasticity has recently been proposed to play an important role, not only for tissue integrity, but also for adipose tissue development, (20, 7, 19). The study of Zdhhc2 is therefore of major interest in light of this emerging concept.

TABLE 1

| Gene name | Biological function and references |
|---|---|
| Acetyl-Coenzyme A dehydrogenase, medium chain (Acadm) | |
| ARP2 actin-related protein 2 homolog (Actr2) | |
| Amyloid beta (A4) precursor protein (App) | |
| Annexin A2 (Anxa2) | Role in actin-assembly |
| Calmodulin 1 (Calm1) | |
| Caveolin, caveolae protein 1 (Cav1) | Role in lipid homeostasis |
| Cyclin G1 (Ccgn1) | |
| Cold shock domain containing E1 (Csde) | |
| Expressed sequence AW112037 | |
| Fibroblast growth factor 1 (Fgf1) | Regulator of human adipogenesis |
| Fibronectin type III domain containing 3B (Fndc3b) | Role in adipogenesis |
| Kinesin family member 5B (Kif5b) | Role in insulin-stimulated GLUT4 translocation to the plasma membrane |
| Mesoderm specific transcript (Mest) | Adipocyte differentiation and enlargement |
| Nucleosome assembly protein 1-like 1 (Nap1L1) | |
| Nidogen 1 (Nid1) | |
| natriuretic peptide receptor 3 (Npr3) | Possible role in sodium retention characteristic of obesity associated hypertension |
| nuclear undecaprenyl pyrophosphate synthase 1 homolog (Nus1) | |
| Phosphatidylinositol 3-kinase, catalytic, alpha polypeptide (Pik3ca) | Essential for proper growth factor signaling. Role in adipogenesis |
| Placenta-specific 8 (Plac8) | |
| Pleckstrin homology domain containing, family C (Plekhc1) | |
| Protein tyrosine phophatase 4a1 (Ptp4a1) | Implicated in cell growth, differentiation, and tumor invasion |
| Related RAS viral (Rras2) oncogene homolog 2 | |
| Retinitis pigmentosa 9 homolog (Rp9h) | |
| Secreted acidic cysteine rich glycoprotein (Sparc) | Mediates cell-matrix interactions and play a differentiation and angiogenesis |
| Signal-induced proliferation-associated 1 like 1 (Sipa1L1) | |
| Spectrin beta 2 (Spnb2) | |
| ST3 beta-galactoside alpha-2,3-sialyltransferase 6 (St3gal6) | |
| Vestigial like 3 (Vgll3) | |
| Very low density lipoprotein receptor (Vldlr) | Involved in lipolysis |
| Zinc finger, DHHC domain containing 2 (Zdhhc2) | |
| WD repeat domain 26 (Wdr26) | |
| WW domain containing transcription regulator 1 (Wwtr1) | regulates mesenchymal stem cell differentiation |
| Expressed sequence AW112037 | |
| RIKEN cDNA B930093H17 gene (like-glycosyltransferase) | |

List of 34 gene candidates regulated by HFD and rimonabant in SCAT and VAT.
The full name and gene symbol are showed in the first column.
The biological role for known genes and references are indicated in the second column.
All these genes were up-regulated by HFD and normalized by rimonabant treatment, excepted for Plac8 and Rp9h, which were down-regulated by HFD.
The genes correlated to body weight increase are shown in grey.

Example 2

Tissue and Cellular Expression of the Selected Genes

To better understand the role of Zdhhc2 in adipocytes development, its pattern of expression was first characterized.

mRNA levels were measured by northern-blot and RT-PCR in various mouse tissues, in isolated preadipocytes and adipocytes, in visceral adipose tissue (VAT) and subcutaneous adipose tissue (SCAT) of mouse obesity model (Ob/Ob mice) and in human adipose tissues.

Figure 2A:
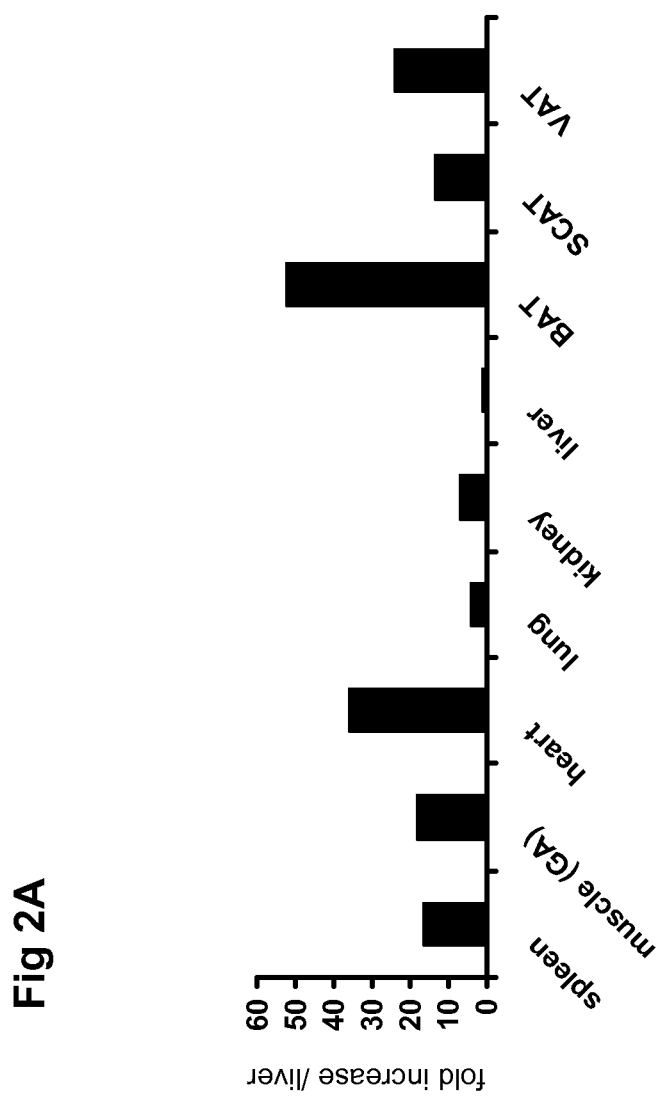
FIG. 2: Zdhhc2 expression in various tissue and cell types A) Analysis of Zdhhc2 expression by RT-PCR for showing mRNA expression in various mouse tissues: spleen, muscle (gastrocnemius), heart, lung, kidney, liver, brown adipose tissue (BAT), subcutaneous (SCAT) and visceral (VAT) adipose tissues; results were normalized by reference to basal expression in liver. B to E: mRNA levels of Zdhhc2 measured by RT-PCR B) in SCAT and VAT of wild-type and Ob/Ob mice (n=5)*p<0.05, data are shown as mean±sd and expressed as fold increase relative to the control SCAT set at 1. C) in SVF and isolated adipocytes of mice (n=5 mice pooled for each extraction, experiment was repeated 3 times, a representative experiment is shown). Data are expressed as fold increase relative to SCAT SVF expression. D) in human whole tissue SCAT and VAT, isolated adipocytes, isolated preadipocytes and adipocytes differentiated in vitro. Data are expressed as levels relative to whole tissue SCAT expression set arbitrary at 1. E) in 3T3-L1 cells prior DMI treatment day-2 and after DMI treatment until day 7. N=3 sets of cells. Data are represented as levels relative to the expression at day 0.
Figure 2B:
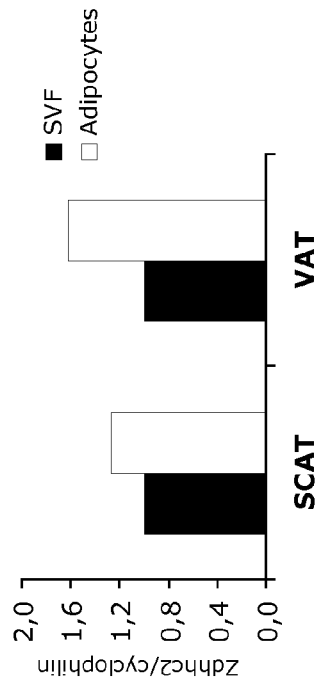

By RT-PCR, it was shown that Zdhhc2 is strongly expressed in heart, BAT, SCAT, VAT spleen and muscle, whereas the expression of Zdhhc2 is weaker in lung and kidney and very weak in liver (FIG. 2A). It was also demonstrated that Zdhhc2 level is increased in white adipose tissues of Ob/Ob mice, compared to level in wild type mice (FIG. 2B). Values are expressed as fold increase relative to the control values in SCAT set arbitrarily at 1.

Figure 2C:
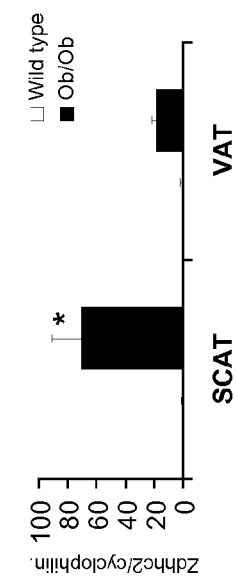

Adipose tissue is a complex tissue that includes not only mature adipocytes, but also precursor cells such as preadipocytes as well as blood vessels, macrophages and fibroblastic cells. Based on a collagenase I digestion technique, stromal vascular fraction (SVF) (including preadipocyte, endothelial and macrophage cells) was separated from the isolated adipocyte fraction. It was found that Zdhhc2 is expressed in both fractions, SVF and isolated adipocytes (FIG. 2C). These results indicate that Zdhhc2 is involved in differentiation and/or proliferation processes but also in immature adipocyte biology.

Figure 2D:
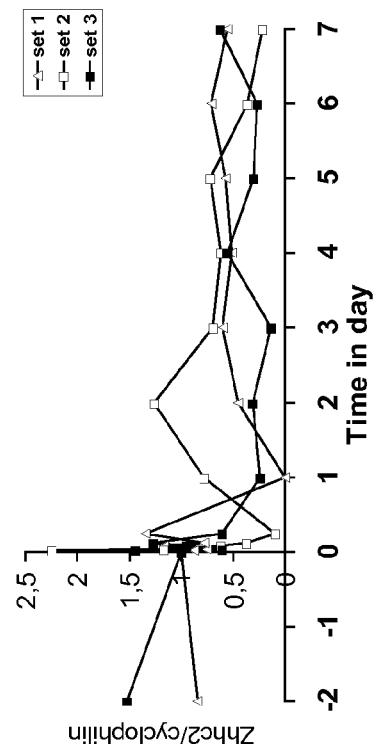

The next step was to determine whether Zdhhc2 gene is conserved among species. To address this question, a RT-PCR was performed on human adipose tissue samples. Preadipocytes and adipocytes were isolated from SCAT or VAT. Isolated preadipocytes were induced to differentiate in vitro until day 7. Results showed that Zdhhc2 is indeed expressed in human fat (FIG. 2D). They indicate that these genes are present in human adipose tissues. Altogether these results suggest that Zdhhc2 is a relevant candidate gene for adipocytes development, especially for adipogenesis or fat tissue enlargement in obesity.

Example 3

Expression of Selected Genes During 3T3-L1 Differentiation

Figure 2E:
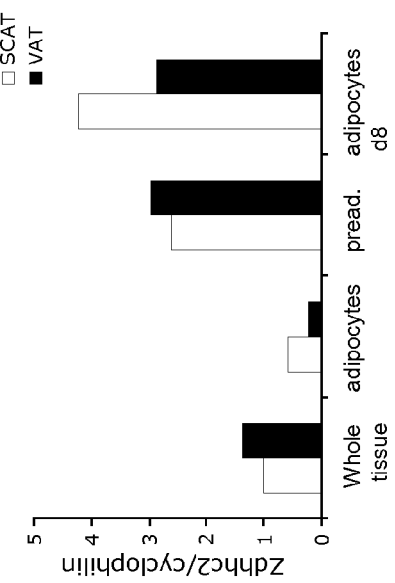

Next, the expression of Zdhhc2 gene was assessed during adipogenesis. For that purpose, mRNA levels were measured by RT-PCR during a detailed differentiation time-course of 3T3-L1 (an adipogenic cell line) (FIG. 2E). The experiment showed that Zdhhc2 expression is induced at very early times after DMI treatment (between 15 minutes-1 hour) and then remains at low levels during the differentiation.

Example 4 shRNA Knockdown of Zdhhc2 in 3T3-L1 Cells Reduces Adipogenesis

Figure 3B:
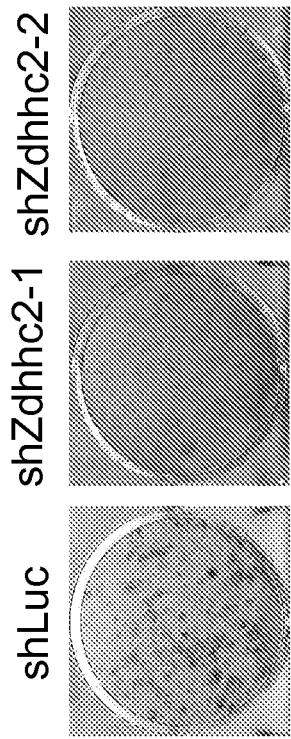
FIG. 3: Knockdown of Zdhhc2 expression and activity by shRNA A) 3T3-L1 cells were transduced with retroviruses containing shRNA directed against luciferase (shLuc) or Zdhhc2 (shZdhhc2). mRNA levels were measured by RT-PCR prior differentiation. B) Oil-red-O pictures of differentiated 3T3-L1 at day 9. C) aP2 (marker of differentiation) mRNA expression measured by RT-PCR in the same cells as in B) at day 9. Results are expressed as mean±sd *P<0.05, **P<0.01, n=3.
Figure 3C:
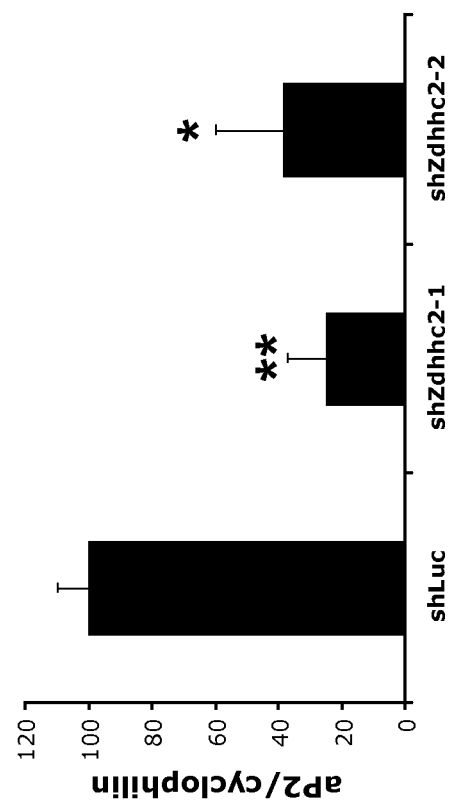

For the loss-of-function studies, shRNA specific for Zdhhc2 subcloned into a retroviral vector from Clontech were used (RNAi-Ready pSIREN-RetroQ ZsGreen or pSIREN). This plasmid contains a GFP marker, which allows controlling the infection efficiency in 3T3-L1 cells. Two different shRNA for Zdhhc2, were cloned into the pSIREN plasmid, and were first tested in 293T HEK cells. This experiment demonstrated the ability of shRNA specific for Zdhhc2 to inhibit Zdhhc2 expression. Interestingly, 60% and 50% of knockdown were obtained respectively with shZdhhc2-1 and shZdhhc2-2 (FIG. 3A), which have been used for transduction into 3T3-L1 cells.

3T3-L1 cells were then infected for 6 hours with retroviral vectors expressing shRNA directed towards either Zdhhc2 (shZdhhc2) or luciferase (shLuc). Using the GFP marker, we observed 90 to 95% infection in the 3T3-L1 cells (data not shown). Then, cells were allowed to reach confluence and to differentiate with DMI treatment. After 9 days of differentiation, cells were stained to determine the amount of lipid content with oil-red-O staining. This experiment evidences that knockdown of Zdhhc2 inhibits adipogenesis in vitro as shown by oil-red-O staining and aP2 expression at day 9 (FIG. 2B), which is decreased by 75 and 60% in ShZdhhc2-1 and shZdhhc2-2 infected 3T3-L1 cells respectively (FIG. 2C). As a control, no inhibition was obtained with shLuc.

BIBLIOGRAPHY

Banerjee, S. S., M. W. Feinberg, M. Watanabe, S. Gray, R. L. Haspel, D. J. Denkinger, R. Kawahara, H. Hauner, and M. K. Jain. 2003. The Kruppel-like factor KLF2 inhibits peroxisome proliferator-activated receptor-gamma expression and adipogenesis. J Biol. Chem. 278: 2581-4. Epub 2002 Nov. 7.

Chen, Z., J. I. Torrens, A. Anand, B. M. Spiegelman, and J. M. Friedman. 2005. Krox20 stimulates adipogenesis via C/EBPbeta-dependent and -independent mechanism. Cell Metab. 2005 February; 1(2): 93-106.

Chun, T. H., K. B. Hotary, F. Sabeh, A. R. Saltiel, E. D. Allen, and S. J. Weiss. 2006. A pericellular collagenase directs the 3-dimensional development of white adipose tissue. Cell 125: 577-91.

Fukumura, D., A. Ushiyama, D. G. Duda, L. Xu, J. Tam, V. Krishna, K. Chatterjee, I. Garkavtsev, and R. K. Jain. 2003. Paracrine regulation of angiogenesis and adipocyte differentiation during in vivo adipogenesis. Circ Res 93: e88-97

Gagnon, A. M., J. Chabot, D. Pardasani, and A. Sorisky. 1998. Extracellular matrix induced by TGFbeta impairs insulin signal transduction in 3T3-L1 preadipose cells. J Cell Physiol 175: 370-8.

Gray, S., M. W. Feinberg, S. Hull, C. T. Kuo, M. Watanabe, S. Sen-Banerjee, A. DePina, R. Haspel, and M. K. Jain. 2002. The Kruppel-like factor KLF15 regulates the insulin-sensitive glucose transporter GLUT4. J Biol Chem 277: 34322-8.

Gregoire, F. M., C. M. Smas, and H. S. Sul. 1998. Understanding adipocyte differentiation. Physiol Rev 78: 783-809.

Hausman, G. J., J. T. Wright, and R. L. Richardson. 1996. The influence of extracellular matrix substrata on preadipocyte development in serum-free cultures of stromal-vascular cells. J Anim Sci 74: 2117-28.

Jimenez, M. A., P. Akerblad, M. Sigvardsson, and E. D. Rosen. 2007. Critical role for Ebf1 and Ebf2 in the adipogenic transcriptional cascade. Mol Cell Biol 27: 743-57.

Jordan M, Wurm F. 2004. Transfection of adherent and suspended cells by calcium phosphate. Methods. 33(2): 136-43

Kang, S., C. N. Bennett, I. Gerin, L. A. Rapp, K. D. Hankenson, and O. A. Macdougald. 2007. Wnt signaling stimulates osteoblastogenesis of mesenchymal precursors by suppressing CCAAT/enhancer-binding protein alpha and peroxisome proliferator-activated receptor gamma. J Biol Chem 282: 14515-24.

Mehlhorn, A. T., P. Niemeyer, S. Kaiser, G. Finkenzeller, G. B. Stark, N. P. Sudkamp, and H. Schmal. 2006. Differential expression pattern of extracellular matrix molecules during chondrogenesis of mesenchymal stem cells from bone marrow and adipose tissue. Tissue Eng 12: 2853-62.

Nakajima, I., S. Muroya, R. Tanabe, and K. Chikuni. 2002. Extracellular matrix development during differentiation into adipocytes with a unique increase in type V and VI collagen. Biol Cell 94: 197-203.

Oyama T, Miyoshi Y, Koyama K, Nakagawa H, Yamori T, Ito T, Matsuda H, Arakawa H, Nakamura Y. 2000. Isolation of a novel gene on 8p21.3-22 whose expression is reduced significantly in human colorectal cancers with liver metastasis. Genes Chromosomes Cancer. September; 29(1): 9-15.

Resh M D. Use of analogs and inhibitors to study the functional significance of protein palmitoylation. Methods. 2006 October; 40(2): 191-7.

Rosen, E. D., C. H. Hsu, X. Wang, S. Sakai, M. W. Freeman, F. J. Gonzalez, and B. M. Spiegelman. 2002. C/EBPalpha induces adipogenesis through PPARgamma: a unified pathway. Genes Dev 16: 22-6.

Sharma C, Yang X H, Hemler M E. DHHC2 affects palmitoylation, stability, and functions of tetraspanins CD9 and CD151. Mol Biol Cell. 2008 August; 19(8): 3415-25.

The invention claimed is:

1. A method for modulating adipogenesis in a patient comprising administering to the patient in need thereof an inhibitor of Zdhhc2 to modulate adipogenesis in the patient, wherein the inhibitor is a double stranded nucleic acid able to mediate RNA interference against Zdhhc2 gene expression.

2. The method of claim 1, wherein adipogenesis is modulated by modulating palmitoylation activity through Zdhhc2 inhibition.

3. The method of claim 2, wherein the modulation of adipogenesis effects treatment of obesity or an obesity-related disorder in the patient.

4. The method of claim 3, wherein the obesity related disorder is selected from the group consisting of type 2 diabetes, dyslipidemia, elevated blood pressure, insulin resistance and metabolic syndrome.

5. The method of claim 2, wherein the modulation of adipogenesis decreases fat accumulation in the patient.

6. A method for modulating adipogenesis in a patient comprising administering to the patient in need thereof an inhibitor of Zdhhc2 to modulate adipogenesis in the patient by modulating palmitoylation activity through Zdhhc2 inhibition, wherein the inhibitor comprises a small interfering RNA against Zdhhc2.

7. A method for modulating adipogenesis in a patient comprising administering to the patient in need thereof an inhibitor of Zdhhc2 to modulate adipogenesis in the patient by modulating palmitoylation activity through Zdhhc2 inhibition, wherein the inhibitor comprises a small interfering RNA against Zdhhc2, and wherein the small interfering RNA is a shRNA having a sequence corresponding to SEQ ID NO. 6.

8. The method of claim 2, wherein the modulation of adipogenesis reduces visceral or subcutaneous fat accumulation in the patient.

9. A method for modulating adipogenesis in a patient comprising administering to the patient in need thereof an inhibitor of Zdhhc2 to modulate adipogenesis in the patient, wherein the inhibitor is a double stranded nucleic acid able to mediate RNA interference against Zdhhc2 gene expression, and wherein the double stranded nucleic acid is a shRNA having a sequence corresponding to SEQ ID NO. 6.

* * * * *

SEQUENCE LISTING

```
<160> NUMBER OF SEQ ID NOS: 17

<210> SEQ ID NO 1
<211> LENGTH: 2498
<212> TYPE: DNA
<213> ORGANISM: Mus musculus
<220> FEATURE:
<221> NAME/KEY: CDS
<222> LOCATION: (229)..(1329)

<400> SEQUENCE: 1
ctactctgag ccgccgcctc agcccggcag agcagcggga gtccgcggcg cccgctcgct      60
gccgcgggat ggggagctag cgccacggcg gccgcggtgg ccgcagcaca gccagccgcc     120 gccccgggc ctgtcccgtc gggtgctccg ggagcccga gccggcccc gagccaggcc        180 cacgggcggc ggcggcggca gagctgggca ggtgtctgcg gctggaag atg gcg ccc      237
                                                    Met Ala Pro
                                                      1 tcg ggc tcg ggc ggc gtg agg cgg cgg tgc cgg cgg gtg ctc tac tgg      285
Ser Gly Ser Gly Gly Val Arg Arg Arg Cys Arg Arg Val Leu Tyr Trp
  5                  10                  15 atc ccg gtg gtg ttc atc agc ttg ctg ctg ggc tgg tcc tac tac gcc      333
Ile Pro Val Val Phe Ile Ser Leu Leu Leu Gly Trp Ser Tyr Tyr Ala
 20                  25                  30                  35 tac gcc atc cag ctg tgc ata gtg tcc atg gaa aac att ggt gaa caa      381
Tyr Ala Ile Gln Leu Cys Ile Val Ser Met Glu Asn Ile Gly Glu Gln
                 40                  45                  50 gtt gtg tgc ctc atg gct tat cat cta ctt ttt gca atg ttt gtc tgg      429
Val Val Cys Leu Met Ala Tyr His Leu Leu Phe Ala Met Phe Val Trp
             55                  60                  65 tca tac tgg aaa acc att ttt aca ttg ccc atg aat cct tca aaa gaa      477
Ser Tyr Trp Lys Thr Ile Phe Thr Leu Pro Met Asn Pro Ser Lys Glu
         70                  75                  80 ttc cat ctc tct tat gca gag aaa gaa ttg ctg gag aga gag cca aga      525
Phe His Leu Ser Tyr Ala Glu Lys Glu Leu Leu Glu Arg Glu Pro Arg
     85                  90                  95 gga gaa gcc cat cag gaa gtt ctg agg cga gca gcc aaa gac ctt ccc      573
Gly Glu Ala His Gln Glu Val Leu Arg Arg Ala Ala Lys Asp Leu Pro
100                 105                 110                 115 atc tac acc agg acc atg tcc ggc gca atc cga tat tgt gac aga tgc      621
Ile Tyr Thr Arg Thr Met Ser Gly Ala Ile Arg Tyr Cys Asp Arg Cys
                120                 125                 130 caa ctt ata aaa cca gac cgc tgt cat cat tgt tcc gtc tgt gat aaa      669
Gln Leu Ile Lys Pro Asp Arg Cys His His Cys Ser Val Cys Asp Lys
            135                 140                 145 tgt att ttg aag atg gat cat cat tgc cca tgg gtg aac aat tgt gtt      717
Cys Ile Leu Lys Met Asp His His Cys Pro Trp Val Asn Asn Cys Val
        150                 155                 160 gga ttt tca aac tac aaa ttc ttc ctt ctt ttc ttg gct tac tct ctg      765
Gly Phe Ser Asn Tyr Lys Phe Phe Leu Leu Phe Leu Ala Tyr Ser Leu
    165                 170                 175
```

```
ctg tac tgc ctt ttc att gct gct acc gat tta cag tat ttt atc aga    813
Leu Tyr Cys Leu Phe Ile Ala Ala Thr Asp Leu Gln Tyr Phe Ile Arg
180                 185                 190                 195 ttt tgg aca aat ggt ctg cct gat act caa gcc aag ttc cat att atg    861
Phe Trp Thr Asn Gly Leu Pro Asp Thr Gln Ala Lys Phe His Ile Met
            200                 205                 210 ttt tta ttc ttt gct gca gct atg ttt tct gtc agc ttg tcc tct ctg    909
Phe Leu Phe Phe Ala Ala Ala Met Phe Ser Val Ser Leu Ser Ser Leu
        215                 220                 225 ttt ggt tat cat tgc tgg cta gtc agc aaa aat aaa tct act tta gag    957
Phe Gly Tyr His Cys Trp Leu Val Ser Lys Asn Lys Ser Thr Leu Glu
    230                 235                 240 gca ttc aga aat cca gta ttt aga cac gga aca gat aag aac gga ttc    1005
Ala Phe Arg Asn Pro Val Phe Arg His Gly Thr Asp Lys Asn Gly Phe
245                 250                 255 agc ttg ggt ttc agt aaa aac atg aga caa gtg ttt ggt gat gag aag    1053
Ser Leu Gly Phe Ser Lys Asn Met Arg Gln Val Phe Gly Asp Glu Lys
260                 265                 270                 275 aaa tac tgg ctg tta cca gta ttt tca agt caa ggt gat ggc tgt tcc    1101
Lys Tyr Trp Leu Leu Pro Val Phe Ser Ser Gln Gly Asp Gly Cys Ser
            280                 285                 290 ttt cca act tgc ctt gtt aac cag gat cct gaa caa cct tct act cct    1149
Phe Pro Thr Cys Leu Val Asn Gln Asp Pro Glu Gln Pro Ser Thr Pro
        295                 300                 305 gcg gga cta aat tca aca gtg aaa aat cct gaa aac cac cag ttt cct    1197
Ala Gly Leu Asn Ser Thr Val Lys Asn Pro Glu Asn His Gln Phe Pro
    310                 315                 320 gca aag cct ctg aga gag tcc cag agc cat ctc ctt aag gat tct cag    1245
Ala Lys Pro Leu Arg Glu Ser Gln Ser His Leu Leu Lys Asp Ser Gln
325                 330                 335 acc tgg aca gag agc agc gca aac cct ggg aag ggc aaa gcc ggt atg    1293
Thr Trp Thr Glu Ser Ser Ala Asn Pro Gly Lys Gly Lys Ala Gly Met
340                 345                 350                 355 agc aac cct gca tta act atg gag aac gag act tag ttctacaatc         1339
Ser Asn Pro Ala Leu Thr Met Glu Asn Glu Thr
                360                 365 aaaataaaac cactcttgta aagtaccagt gctgtggagg aatggaacaa ccttccgatt  1399
ggaaggcacc atttgccaat tgtccctata tcccttgac tagatatgca aattttgtct   1459
tcagtgatgg ggatcaaaca cagcagtatg aagagtttca agtaatcacc aaactgatgc  1519
ttaaaacaga acactgttta ttccaatata taaacttctg taactaatac aaattactat  1579
taacctttaa aagttattaa aagggaacca ttttctgcca aaacccgaga ttaagtttat  1639
gggcccatgt tcattcgaat aattgggttg tacaacttat ctcataatcc cattattcat  1699
ttgatattct gttttagaaa atttaggtta atcttaagat ttaataaatt tcaaatcatg  1759
ttattatgca aaactgtatt tgagagcagg taagaaatca tccttgattt ttttttttctg 1819 atgtgagatt agcttccgat gagagagctg cattgactat gaactcatta cggaggccat  1879
gtagcctata gctggaggtc atttatcccc ttgtgccagg tttcaattcc cattctagac  1939
tttgtctccc attggaagat tcaaatacaa atactgaagc tcgagttcaa agcaattgga  1999
taaaactttt tgtttgactt aatatgatgt cttgacaagg aacttacatc agaaatgtac  2059
tttcatgtct tctcatttga aatcagaggg aacacatgct aattctcttg aagattgcct  2119
ggcaacactc ttttgctggt ttggatgtta accaatctgt ttttttttttt taactacttg  2179 ctcagtgtta ttgtgaaaag actgagtttc taagcatttc tgatagatca atggattatt  2239
```

```
cctccatgtg cacctgtgta tcatctctgt cttttcatca aaactacaat tgtcaataga   2299 tattttcct caaatgccta tccagattaa attatgcaaa tcatttaaaa atgaggaagt    2359
ttagtttacc atgaactaaa catcgtgctg tttagaaatg tagtttaggg taaattacga   2419
taatgtgttt gttgatgcca aaatgtttgg cctcagtaag tatactcaca gaagttcttg   2479
tgccttgtat gcactattt                                                2498
```

```
<210> SEQ ID NO 2
<211> LENGTH: 366
<212> TYPE: PRT
<213> ORGANISM: Mus musculus

<400> SEQUENCE: 2

Met Ala Pro Ser Gly Ser Gly Gly Val Arg Arg Cys Arg Arg Val
1               5                   10                  15

Leu Tyr Trp Ile Pro Val Val Phe Ile Ser Leu Leu Gly Trp Ser
                20                  25                  30

Tyr Tyr Ala Tyr Ala Ile Gln Leu Cys Ile Val Ser Met Glu Asn Ile
                35                  40                  45

Gly Glu Gln Val Val Cys Leu Met Ala Tyr His Leu Leu Phe Ala Met
50                  55                  60

Phe Val Trp Ser Tyr Trp Lys Thr Ile Phe Thr Leu Pro Met Asn Pro
65                  70                  75                  80

Ser Lys Glu Phe His Leu Ser Tyr Ala Glu Lys Glu Leu Leu Glu Arg
                85                  90                  95

Glu Pro Arg Gly Glu Ala His Gln Glu Val Leu Arg Arg Ala Ala Lys
            100                 105                 110

Asp Leu Pro Ile Tyr Thr Arg Thr Met Ser Gly Ala Ile Arg Tyr Cys
        115                 120                 125

Asp Arg Cys Gln Leu Ile Lys Pro Asp Arg Cys His His Cys Ser Val
130                 135                 140

Cys Asp Lys Cys Ile Leu Lys Met Asp His His Cys Pro Trp Val Asn
145                 150                 155                 160

Asn Cys Val Gly Phe Ser Asn Tyr Lys Phe Phe Leu Leu Phe Leu Ala
                165                 170                 175

Tyr Ser Leu Leu Tyr Cys Leu Phe Ile Ala Ala Thr Asp Leu Gln Tyr
            180                 185                 190

Phe Ile Arg Phe Trp Thr Asn Gly Leu Pro Asp Thr Gln Ala Lys Phe
        195                 200                 205

His Ile Met Phe Leu Phe Ala Ala Ala Met Phe Ser Val Ser Leu
210                 215                 220

Ser Ser Leu Phe Gly Tyr His Cys Trp Leu Val Ser Lys Asn Lys Ser
225                 230                 235                 240

Thr Leu Glu Ala Phe Arg Asn Pro Val Phe Arg His Gly Thr Asp Lys
                245                 250                 255

Asn Gly Phe Ser Leu Gly Phe Ser Lys Asn Met Arg Gln Val Phe Gly
            260                 265                 270

Asp Glu Lys Lys Tyr Trp Leu Leu Pro Val Phe Ser Ser Gln Gly Asp
        275                 280                 285

Gly Cys Ser Phe Pro Thr Cys Leu Val Asn Gln Asp Pro Glu Gln Pro
290                 295                 300

Ser Thr Pro Ala Gly Leu Asn Ser Thr Val Lys Asn Pro Glu Asn His
305                 310                 315                 320

Gln Phe Pro Ala Lys Pro Leu Arg Glu Ser Gln Ser His Leu Leu Lys
```

```
                    325                 330                 335
Asp Ser Gln Thr Trp Thr Glu Ser Ser Ala Asn Pro Gly Lys Gly Lys
                340                 345                 350

Ala Gly Met Ser Asn Pro Ala Leu Thr Met Glu Asn Glu Thr
            355                 360                 365

<210> SEQ ID NO 3
<211> LENGTH: 3832
<212> TYPE: DNA
<213> ORGANISM: Homo sapiens
<220> FEATURE:
<221> NAME/KEY: CDS
<222> LOCATION: (203)..(1306)

<400> SEQUENCE: 3
gccgggctga ggagccggga gtccgccgcg ccggctcggg gctgcgggat ggggagttag      60
cgccacggcg gcggcagtgg ccgcagcgca ccccgccgcc gcccaggagc ccgtccagcc     120
aggggtgccg ggcccgccca gcccgccccg gagccaggcc cgcgggcggc ggcggagctg     180
ggcaggtgga tgcggctgga ag atg gcg ccc tcg ggc ccg ggc agc agc gcc     232
                         Met Ala Pro Ser Gly Pro Gly Ser Ser Ala
                           1               5                  10 agg cgg cgg tgc cgg cgg gtg ctg tac tgg atc ccg gtg gtg ttc atc     280
Arg Arg Arg Cys Arg Arg Val Leu Tyr Trp Ile Pro Val Val Phe Ile
             15                  20                  25 acc ctc ctg ctc ggc tgg tcc tac tac gcc tac gcc atc cag ctg tgc     328
Thr Leu Leu Leu Gly Trp Ser Tyr Tyr Ala Tyr Ala Ile Gln Leu Cys
         30                  35                  40 ata gtg tcc atg gaa aac act ggc gaa caa gtt gtg tgc ctg atg gcc     376
Ile Val Ser Met Glu Asn Thr Gly Glu Gln Val Val Cys Leu Met Ala
     45                  50                  55 tat cat cta ctt ttt gca atg ttt gtc tgg tca tac tgg aaa act atc     424
Tyr His Leu Leu Phe Ala Met Phe Val Trp Ser Tyr Trp Lys Thr Ile
 60                  65                  70 ttt aca tta cca atg aat cct tca aaa gaa ttc cat ctc tct tat gca     472
Phe Thr Leu Pro Met Asn Pro Ser Lys Glu Phe His Leu Ser Tyr Ala
75                  80                  85                  90 gag aaa gat ttg ttg gag aga gag cca aga gga gaa gcc cat cag gaa     520
Glu Lys Asp Leu Leu Glu Arg Glu Pro Arg Gly Glu Ala His Gln Glu
                 95                 100                 105 gtt ctt agg cga gca gcc aag gat ctt ccc atc tat acc agg acc atg     568
Val Leu Arg Arg Ala Ala Lys Asp Leu Pro Ile Tyr Thr Arg Thr Met
            110                 115                 120 tct gga gcc atc cga tac tgt gac aga tgc caa ctt ata aaa cca gat     616
Ser Gly Ala Ile Arg Tyr Cys Asp Arg Cys Gln Leu Ile Lys Pro Asp
        125                 130                 135 cgc tgc cat cac tgc tcc gtc tgt gat aaa tgt att ttg aag atg gat     664
Arg Cys His His Cys Ser Val Cys Asp Lys Cys Ile Leu Lys Met Asp
    140                 145                 150 cat cat tgt cca tgg gtg aac aat tgt gtt gga ttt tca aat tat aag     712
His His Cys Pro Trp Val Asn Asn Cys Val Gly Phe Ser Asn Tyr Lys
155                 160                 165                 170 ttc ttt ctc ctt ttc ttg gct tat tct ctg ctc tac tgc ctt ttt att     760
Phe Phe Leu Leu Phe Leu Ala Tyr Ser Leu Leu Tyr Cys Leu Phe Ile
                175                 180                 185 gcg gca aca gat tta cag tat ttt atc aaa ttt tgg aca aat ggc cta     808
Ala Ala Thr Asp Leu Gln Tyr Phe Ile Lys Phe Trp Thr Asn Gly Leu
            190                 195                 200 cct gat act caa gcc aag ttc cat att atg ttt tta ttc ttt gct gca     856
Pro Asp Thr Gln Ala Lys Phe His Ile Met Phe Leu Phe Phe Ala Ala
```

```
                  205                 210                 215
gct atg ttt tct gtc agc ttg tct tct ctg ttt ggc tat cat tgt tgg     904
Ala Met Phe Ser Val Ser Leu Ser Ser Leu Phe Gly Tyr His Cys Trp
    220                 225                 230 cta gtc agc aaa aat aaa tct aca tta gag gca ttc aga agt cca gta     952
Leu Val Ser Lys Asn Lys Ser Thr Leu Glu Ala Phe Arg Ser Pro Val
235                 240                 245                 250 ttt cga cat gga aca gat aag aat gga ttc agc ttg ggt ttc agt aaa    1000
Phe Arg His Gly Thr Asp Lys Asn Gly Phe Ser Leu Gly Phe Ser Lys
                255                 260                 265 aac atg cga caa gtt ttt ggt gat gag aag aag tac tgg ttg cta ccc    1048
Asn Met Arg Gln Val Phe Gly Asp Glu Lys Lys Tyr Trp Leu Leu Pro
            270                 275                 280 att ttt tca agt cta ggt gat ggc tgc tcc ttt cca act tgc ctt gtt    1096
Ile Phe Ser Ser Leu Gly Asp Gly Cys Ser Phe Pro Thr Cys Leu Val
        285                 290                 295 aac cag gat cct gaa caa gca tct act cct gca ggg ctg aat tcc aca    1144
Asn Gln Asp Pro Glu Gln Ala Ser Thr Pro Ala Gly Leu Asn Ser Thr
    300                 305                 310 gct aaa aat ctc gaa aac cat cag ttt cct gca aag cca ttg aga gag    1192
Ala Lys Asn Leu Glu Asn His Gln Phe Pro Ala Lys Pro Leu Arg Glu
315                 320                 325                 330 tcc cag agc cac ctt ctt act gat tct cag tct tgg acg gag agc agc    1240
Ser Gln Ser His Leu Leu Thr Asp Ser Gln Ser Trp Thr Glu Ser Ser
                335                 340                 345 ata aac cca gga aaa tgc aaa gct ggt atg agc aat cct gca tta acc    1288
Ile Asn Pro Gly Lys Cys Lys Ala Gly Met Ser Asn Pro Ala Leu Thr
            350                 355                 360 atg gaa aat gag act taa ctcttcaagc aagataaatt catactttat           1336
Met Glu Asn Glu Thr
            365 aaaagtatca atgctgtaga tggatggaag aggcttccca caggaaggtg ccaccagtca  1396
gttgtgccta tgtccctttg gctggaaatg cagaatatga attgattagt tctctccaag  1456
ccattgctta aaatataaca tgttttggat ccaatacaca cattgttaca actaacacaa  1516
attcctatta aatattaaaa gtagttctgg tttattaatc aacggggaaa acatcttctc  1576
caaaaaactt ggaataaatc caaggaccag ttttacccca aatatatggg tagcacagtt  1636
tatcacatag aaactccatt aatcatctga ttttccgaat ctgaaaattg agactattaa  1696
gatattaaga tttcagagat ttcaagtcac attataatga taagcattat tcataaaact  1756
tgttaccttt aagaaggtgg aagtggcaaa ccatacttct ttttttttcc tctgatgtga  1816
atccagcctc agactgagtg aactgtaata attatgaatt cattacagag tccaggtggc  1876
ctgcagttga agatcatcaa ccattttgtc ctcacttaat tccagccttt tgttttctgc  1936
tggaaaataa gtgtggacat tgaagcttga gctctcaaag cagttggctg gaatactttt  1996
gtcagaatac ggtacatttc tattacatca gaaatatatt ttcatctctt cttgttaaat  2056
tgggaggaaa tttatgatag caattatgaa gattgtttta tgacattctt ttgtcagttt  2116
ggctttctaa aaatctcttt ttagattatt tctcctgttg aacatagtaa aactattgaa  2176
tttctcttaa gaattcctaa taggtcaata gatttaccct ccagtgatat ctatattatt  2236
tctttctcgt ctcatcaaaa tgatgacagg taaactatat ttttccttaa acacctatta  2296
cagttaaatt atgcaaatca ttaaataaaa atcatacaac ttttggaaag ttagttcaac  2356
atgaactaaa atggcatgct atttggaaat ttagttgag ataaactaaa gtgtgttgat   2416
gccagaatgt tcagcttcag taaatataat aagctcttgt gccttgtatg cactatttaa  2476
```

```
aaaaagtttt ttttatttga gtccagtata attcatgtaa atgttaacaa ttagaataat    2536
actctgtatg ctttttttgat actgattttg agaatttaaa gcagattacc ttttaaaact    2596
ggaccaacta agtaattggt atttaatcaa agagaaaatg gtaataaact tttcaaaatc    2656
tttgttaaac caaacattca acacaaaata aactagaagg ccagaggata atggaataaa    2716
agatcattgc aattacttat ccttcctaaa aatatagttt tatattaatt gtgcttatgg    2776
aagaaacaat gtcagccaag tccattttat agtttgagtg caattctttg aacaatagaa    2836
atatctgcag tctttcacag atttgtatta tgctgaagag tttcatctga caatctgctt    2896
caagaaatct cagaaaatat gataacattt taactttcgt tttagagcac gttttggtca    2956
tttttaaaaa tacctaaagt gccagaccgg aacctatagc tactgctaga agtcttaaaa    3016
aaaccaacag cagcacagga tgtattaaga attatatgaa gtcaggtttg ttttttttttt    3076 ttttttttc aaagcacagt actgttagct gtttttgtgg acaggattcg attaagtatt    3136
ccctcttgtc aaactggaag ctaggggaaa aagagggatt tttatccttt actcttctag    3196
agtactgtta atgccccttt cccacagtct tttatataat taaatatatg tcaatacaca    3256
ttagaatcag atttgaaaaa gttaaaacaa tttcattgtt gtaattgttc cctttctgtt    3316
ttcatatagt gaataacctt taaagggttg ttttgttttg ttttgaatta taggagttat    3376
aatctttgga gatgattgca tatctcatta gatatgcaat ataaatttat ctgagtgaac    3436
aaagtgctaa ataaatagat ctacattttg tacatattta tataaaattt acctttaagt    3496
atttacttta aaaaatttaa tggcttaact cgaacttgaa gacacatact tcaactgtcc    3556
ttattgtcca ttaaactgat aattttgatt tttcttgctt ttatagattt tactatatag    3616
gaatcaagat ttagaaaatt ttgcattaaa aatagtgtac caatgcttca tatacgttag    3676
ttatttgcta ttatgtaggg aagaggattg ttatttcaaa gatatattaa agaacagttg    3736
catctgaata taatcatgat gcattcaatg aagttcatat ccatgaattc actcctaata    3796
taccctaata aagtggttga aaccgaaaaa aaaaaa                              3832
```

<210> SEQ ID NO 4
<211> LENGTH: 367
<212> TYPE: PRT
<213> ORGANISM: Homo sapiens

<400> SEQUENCE: 4

```
Met Ala Pro Ser Gly Pro Gly Ser Ser Ala Arg Arg Cys Arg Arg
1               5                   10                  15

Val Leu Tyr Trp Ile Pro Val Val Phe Ile Thr Leu Leu Gly Trp
                20                  25                  30

Ser Tyr Tyr Ala Tyr Ala Ile Gln Leu Cys Ile Val Ser Met Glu Asn
                35                  40                  45

Thr Gly Glu Gln Val Val Cys Leu Met Ala Tyr His Leu Leu Phe Ala
    50                  55                  60

Met Phe Val Trp Ser Tyr Trp Lys Thr Ile Thr Leu Pro Met Asn
65                  70                  75                  80

Pro Ser Lys Glu Phe His Leu Ser Tyr Ala Glu Lys Asp Leu Leu Glu
                85                  90                  95

Arg Glu Pro Arg Gly Glu Ala His Gln Glu Val Leu Arg Arg Ala Ala
                100                 105                 110

Lys Asp Leu Pro Ile Tyr Thr Arg Thr Met Ser Gly Ala Ile Arg Tyr
                115                 120                 125
```

```
Cys Asp Arg Cys Gln Leu Ile Lys Pro Asp Arg Cys His His Cys Ser
            130                 135                 140

Val Cys Asp Lys Cys Ile Leu Lys Met Asp His His Cys Pro Trp Val
145                 150                 155                 160

Asn Asn Cys Val Gly Phe Ser Asn Tyr Lys Phe Phe Leu Leu Phe Leu
                165                 170                 175

Ala Tyr Ser Leu Leu Tyr Cys Leu Phe Ile Ala Ala Thr Asp Leu Gln
                180                 185                 190

Tyr Phe Ile Lys Phe Trp Thr Asn Gly Leu Pro Asp Thr Gln Ala Lys
                195                 200                 205

Phe His Ile Met Phe Leu Phe Ala Ala Ala Met Phe Ser Val Ser
            210                 215                 220

Leu Ser Ser Leu Phe Gly Tyr His Cys Trp Leu Val Ser Lys Asn Lys
225                 230                 235                 240

Ser Thr Leu Glu Ala Phe Arg Ser Pro Val Phe Arg His Gly Thr Asp
                245                 250                 255

Lys Asn Gly Phe Ser Leu Gly Phe Ser Lys Asn Met Arg Gln Val Phe
                260                 265                 270

Gly Asp Glu Lys Lys Tyr Trp Leu Leu Pro Ile Phe Ser Ser Leu Gly
            275                 280                 285

Asp Gly Cys Ser Phe Pro Thr Cys Leu Val Asn Gln Asp Pro Glu Gln
            290                 295                 300

Ala Ser Thr Pro Ala Gly Leu Asn Ser Thr Ala Lys Asn Leu Glu Asn
305                 310                 315                 320

His Gln Phe Pro Ala Lys Pro Leu Arg Glu Ser Gln Ser His Leu Leu
                325                 330                 335

Thr Asp Ser Gln Ser Trp Thr Glu Ser Ser Ile Asn Pro Gly Lys Cys
                340                 345                 350

Lys Ala Gly Met Ser Asn Pro Ala Leu Thr Met Glu Asn Glu Thr
                355                 360                 365

<210> SEQ ID NO 5
<211> LENGTH: 65
<212> TYPE: DNA
<213> ORGANISM: Artificial
<220> FEATURE:
<223> OTHER INFORMATION: scRNA
<220> FEATURE:
<221> NAME/KEY: misc_RNA
<222> LOCATION: (1)..(65)
<223> OTHER INFORMATION: shZdhhc2-1

<400> SEQUENCE: 5
gatccaggtg atggctgttc cttttttcaag agaaaaggaa cagccatcac ctttttttac    60
gcgtg                                                                 65

<210> SEQ ID NO 6
<211> LENGTH: 63
<212> TYPE: DNA
<213> ORGANISM: Artificial
<220> FEATURE:
<223> OTHER INFORMATION: shZdhhc2-2

<400> SEQUENCE: 6
gatccgtatg agcaaccctg catttcaaga gaatgcaggg ttgctcatac ttttttacgc    60
gtg                                                                   63

<210> SEQ ID NO 7
```

-continued

<210> SEQ ID NO 7
<211> LENGTH: 63
<212> TYPE: DNA
<213> ORGANISM: Artificial
<220> FEATURE:
<223> OTHER INFORMATION: shLuc

<400> SEQUENCE: 7
gatccgtgcg ttgctagtac caattcaaga gattggtact agcaacgcac ttttttacgc   60
gtg   63

<210> SEQ ID NO 8
<211> LENGTH: 18
<212> TYPE: DNA
<213> ORGANISM: Artificial
<220> FEATURE:
<223> OTHER INFORMATION: Primer mZdhhc2-F

<400> SEQUENCE: 8
ggatcccggt ggtgttca   18

<210> SEQ ID NO 9
<211> LENGTH: 20
<212> TYPE: DNA
<213> ORGANISM: Artificial
<220> FEATURE:
<223> OTHER INFORMATION: Primer mZdhhc2-R

<400> SEQUENCE: 9
ctggatggcg taggcgtagt   20

<210> SEQ ID NO 10
<211> LENGTH: 20
<212> TYPE: DNA
<213> ORGANISM: Artificial
<220> FEATURE:
<223> OTHER INFORMATION: Primer hZdhhc2-F

<400> SEQUENCE: 10
tggacggaga gcagcataaa   20

<210> SEQ ID NO 11
<211> LENGTH: 21
<212> TYPE: DNA
<213> ORGANISM: Artificial
<220> FEATURE:
<223> OTHER INFORMATION: Primer hZdhhc2-R

<400> SEQUENCE: 11
ccatggttaa tgcaggattg c   21

<210> SEQ ID NO 12
<211> LENGTH: 20
<212> TYPE: DNA
<213> ORGANISM: Artificial
<220> FEATURE:
<223> OTHER INFORMATION: Primer mCyclophilin A-F

<400> SEQUENCE: 12
ttttgacttg cgggcatttt   20

<210> SEQ ID NO 13
<211> LENGTH: 22
<212> TYPE: DNA
<213> ORGANISM: Artificial
<220> FEATURE:
<223> OTHER INFORMATION: Primer mCyclophilin A-R

```
<400> SEQUENCE: 13
ggacgctctc ctgagctaca ga                                              22

<210> SEQ ID NO 14
<211> LENGTH: 20
<212> TYPE: DNA
<213> ORGANISM: Artificial
<220> FEATURE:
<223> OTHER INFORMATION: Primer hCyclophilin A-F

<400> SEQUENCE: 14
ttcatctgca ctgccaagac                                                 20

<210> SEQ ID NO 15
<211> LENGTH: 20
<212> TYPE: DNA
<213> ORGANISM: Artificial
<220> FEATURE:
<223> OTHER INFORMATION: Primer hCyclophilin A-R

<400> SEQUENCE: 15
tcgagttgtc cacagtcagc                                                 20

<210> SEQ ID NO 16
<211> LENGTH: 19
<212> TYPE: DNA
<213> ORGANISM: Artificial
<220> FEATURE:
<223> OTHER INFORMATION: Primer Ap2-F

<400> SEQUENCE: 16
ccgcagacga caggaaggt                                                  19

<210> SEQ ID NO 17
<211> LENGTH: 15
<212> TYPE: DNA
<213> ORGANISM: Artificial
<220> FEATURE:
<223> OTHER INFORMATION: Primer Ap2-R

<400> SEQUENCE: 17
agggccccgc catct                                                      15
```